United States Patent [19]

Gignier et al.

[11] 4,175,192
[45] Nov. 20, 1979

[54] PROCESS FOR PREPARING QUININONE

[76] Inventors: Jean P. Gignier, 4 Rue de Capucins; Jacques Bourrelly, 4 Ave. de Chateau, both of 92190, Meudom, France

[21] Appl. No.: 915,009

[22] Filed: Jun. 13, 1978

[51] Int. Cl.$^2$ .......................................... C07D 453/04
[52] U.S. Cl. ................................................. 546/134
[58] Field of Search .... 260/284, 288 CE, 586 P (U.S. only); 546/134

[56] References Cited

U.S. PATENT DOCUMENTS

| | | | |
|---|---|---|---|
| 3,444,216 | 5/1969 | Parikh et al. | 260/397.45 |
| 3,551,497 | 12/1970 | Wymore | 260/592 |
| 4,093,619 | 6/1978 | Jarreau et al. | 260/284 |

OTHER PUBLICATIONS

Bent, et al., J. Am. Chem. Soc., vol. 66, 969–973 (1944).
Woodward, et al., J. Am. Chem. Soc., vol. 67, 1425–1429 (1945).
Warnhoff, et al., J. Org. Chem., vol. 28, 1431–1433 (1963).

*Primary Examiner*—Donald G. Daus
*Assistant Examiner*—Diana G. Rivers
*Attorney, Agent, or Firm*—Thomas R. Boland

[57] ABSTRACT

Amino secondary alcohols, e.g. cinchona alkaloid such as quinine, epiquinine, quinidine, epiquinidine and mixtures thereof, are oxidized to quininone, i.e., a mixture of quininone and quinidinone, by reaction of the alcohols with a metal ketyl, in an inert hydrocarbon solvent. The ketyl is formed through the reaction of an alkali metal or amalgam with a diphenyl ketone, such as benzophenone or fluorenone.

18 Claims, No Drawings

PROCESS FOR PREPARING QUININONE

BACKGROUND OF THE INVENTION

This invention relates to a process for oxidizing amino secondary alcohols to corresponding ketones. More particularly, the invention pertains to the conversion of guinine, or derivatives thereof, to quininone in high yield, with a substantial absence of by-products and impurities. The invention concerns a process which dispenses with the conventional use of alcoholates according to modified Oppenhauer methods.

Various methods for the conversion of the cinchona alkaloids to corresponding ketones, and in particular methods for the oxidation of quinine to quininone, are known in the art. One of the earliest methods concerned the use of acidic reagents, e.g., chromic acid, to achieve such an oxidation, but the yield of quininone was so small as to make it impractical for most uses (see, Rabe, P., et al., *Ann.*, 364, 346 (1909)). In 1945, Woodward, et al., (Woodward, R. B., et al., *J. Am. Chem. Soc.*, 67, 1425 (1945)) attempted the use of the Oppenhauer method to effect oxidation of quinine, but upon finding that the use of the conventional aluminum alcoholate as a catalyst was ineffective in achieving the desired conversion, they modified the Oppenhauer method by using potassium t-butylate as the catalyst. They were able to achieve a quantitative oxidation by boiling quinine along with the alkoxide catalyst and benzophenone in benzene. Warnhoff et al suggested later (Warnhoff, E. W., et al., *J. Org. Chem.*, 28, 1431 (1963)) that the quinine to quininone conversion would proceed more rapidly if the hydride acceptor was fluorenone in benzene instead of the benzophenone used by Woodward, et al.

In all of these methods of recent years, one common theme is found in the use of an alkoxide catalyst to achieve the desired oxidation reaction. While these processes have been effective in achieving an acceptable yield of quininone, since alcoholates are used, they enter into the reaction causing the formation of a number of by-products and impurities which must ultimately be removed by expensive purification treatments.

By means of the present invention, the problems generated by the prior art processes have been resolved since it is no longer necessary to employ alcoholates in the oxidation of quinine or its derivatives to quininone.

SUMMARY OF THE INVENTION

According to this invention, a process is provided for oxidizing an amino secondary alcohol to the corresponding ketone by reacting the secondary alcohol with an alkali metal ketyl in an inert solvent. Specifically, an amino secondary alcohol selected from the group consisting of quinine, quinidine, epiquinine, epiquinidine and mixtures thereof is oxidized to quininone by reacting the secondary alcohol with a ketyl which is the reaction product of an alkali metal or amalgam and diaryl ketone.

In the preferred embodiment, the ketyl will be the reaction product of a monovalent alkali metal, such as sodium, potassium, and lithium, and a diphenyl ketone, such as benzophenone or fluorenone. The oxidation is achieved by refluxing at least about stoichiometric quantities of the secondary alcohol, e.g. quinine, and the alkali metal ketyl in an aromatic hydrocarbon solvent, at atmospheric pressure. The metal ketyl may be prepared in situ or formed separately and then included in the reaction mixture to achieve the desired oxidation.

DECRIPTION OF THE PREFERRED EMBODIMENT

As stated above, this invention relates to the oxidation of amino secondary alcohols, especially cinchona alkaloids such as quinine, quinidine, epiquinine and epiquinidine through the reaction of such amino secondary alcohols with a metal ketyl in an inert hydrocarbon solvent.

Metal ketyls, as such, are known and discussed in the literature (see for example, Bent, et al., *J. Am. Chem. Soc.*, 66, 969 (1944); see also *Chemistry of Organic Compounds*, pg. 570). In general such ketyls are prepared by allowing an aryl ketone, such as benzophenone, to react with an alkali metal under anhydrous conditions and in the absence of air. In the preferred embodiment utilized in this invention, a diphenyl ketone, such as benzophenone or fluorenone, is reacted with at least one mole of metallic sodium for each mole of ketyl required. The reaction proceeds in inert hydrocarbon solvent under anhydrous conditions, preferably in refluxing benzene, toluene or xylene. Alternatively, the ketyl may be formed by reacting a diphenyl ketone with an amalgam, such as, for example, sodium amalgam.

It has been shown that the radical anion of the ketyl exhibits a tautomerism between two principle forms. For example, the benzophenone ketyl exhibits the following forms:

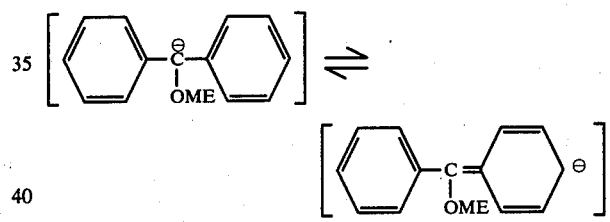

In the case of fluorenone, an analagous equilibrium is established as follows:

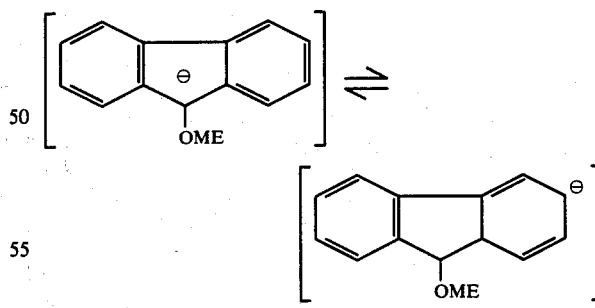

The metal ketyl is mixed with the amino secondary alcohol or a mixture of such secondary alcohols including quinine, quinidine and the epi-bases, i.e., epiquinine and epiquinidine, in at least about stoichiometric quantities, and refluxed in an inert hydrocarbon solvent which may be, for example, $C_6$–$C_9$ aromatic hydrocarbon solvents, $C_6$–$C_9$ aliphatic cyclic hydrocarbon solvents, or aliphatic acyclic hydrocarbons corresponding to a naphtha or gas-oil cut. Preferably the reaction will be carried out under anhydrous conditions.

The resulting quininone product has been shown by recent studies to exhibit mutarotation in solution. It is often recovered as an oily mixture of two isomers, namely quininone and quinidinone but, as indicated in U.S. Pat. No. 3,753,992, quinidinone is the only crystalline form having a melting point of 98°-101° C., whereas quininone can only be isolated in the form of an oil. Thus, quinidinone can be easily extracted through crystallization. Accordingly, unless otherwise indicated, when used in this disclosure the term quninone will relate to an equilibrium mixture of quininone and quinidinone.

The following examples will further illustrate the invention, and unless otherwise indicated all amounts or proportions will be by weight.

EXAMPLE I 2.4 g. of sodium was suspended in 40 ml. of anhydrous, refluxing xylene in order to obtain a good dispersion. After cooling to 90° C., 36 g. of anhydrous benzophenone was slowly added. The solution then turned blue-green, which is characteristic of the ketyl (presence of electrons).

In a second reactor, 13 g. of anhydrous quinine base was dissolved in 50 ml. of boiling xylene. This solution was poured into the previously prepared ketyl solution, and after 60 minutes at reflux the reaction was complete. This reaction solution was then treated with 20 ml. of water and extracted with 100 ml. of sulfuric acid (diluted to 20%). The resulting cold sulfuric acid solution was neutralized by adding ammonia. An oil separated which crystallized slowly after seeding, giving a yield of 12.2 g. (94% of theory). Analysis with Thin Layer Chromatography (TLC) showed: 1 spot, $R_f$: 0.8. (Eluant: acetone 80/DMF 20)

EXAMPLE II 24 g. of sodium was suspended in 40 ml. of anhydrous toluene with heating to obtain finely divided metal by fusion. At the same time 360 g. of anhydrous benzophenone was dissolved in 450 ml. of dry toluene. These two solutions were mixed and kept at reflux for 15 minutes to produce a benzophenone ketyl solution.

130 g. of anhydrous quinine base was dissolved in 500 ml. of boiling anhydrous toluene, and this solution was added while hot to the solution of benzophenone ketyl. After 30 minutes reflux the reaction was complete. The reaction solution was cooled to 50° C., washed with water, and then extracted with 700 ml. of dilute sulfuric acid. The resultant cold sulfuric acid solution was neutralized by the addition of ammonia, yielding 124 g. of an oil which was separated and crystallized by seeding. The resulting product had a melting point of 102° C. and Thin Layer Chromatography reading: 1 spot, $R_f$: 0.8.

EXAMPLE III

To a solution of fluorenone ketyl, prepared by mixing 180 g. of fluorenone and 130 g. of sodium in anhydrous toluene, was added 65 grams of an anhydrous toluene solution containing an alkaloid mixture of the following composition:

| | |
|---|---|
| epiquinine | 35% |
| epiquinidine | 24% |
| quinine | 7% |
| quinidine | 3% |
| quininone | 2% |
| quinotoxine | 2% |
| epicinchonine + epicinchonidine | 12% |
| various alkaloids + other cinchonines | 15% |

The mixed solutions were kept at reflux for a period of 5 hours at the end of which time the reaction was complete. After extraction and neutralization procedures as described in Example I, 55 g. of a product was obtained which contained 39 g. of quininone/quinidinone and 16 g. of cinchoninone/cinchonidinone.

EXAMPLE IV

A solution of fluorenone ketyl was prepared by mixing 9 g. of fluorenone and 6.5 g. of sodium in anhydrous toluene. To this solution was added a hot solution of 37 g. of anhydrous quinidine base in 150 ml. of anhydrous toluene. After 15 minutes at reflux, the reaction was complete. After extraction and neutralization treatments as in Example I, 36 g. of pure quinidinone (TLC) was obtained (97% of theory).

It is thus apparent that the present invention represents a significant advancement in the art in that while achieving excellent yields of quininone, i.e. quininone and quinidinone, it dispenses with the conventionally required, expensive and dangerous alcoholate and avoids the need for recycling in order to eliminate unwanted by-products and impurities. The resulting products are particularly useful as intermediates in the stereospecific reduction of quinidinone to quinidine.

This invention may be embodied in specific forms other than those described without departing from the spirit or the essential characteristics of the invention. Therefore, the present embodiments are to be considered in all respects as illustrative and not restrictive, the scope of the invention being indicated by the appended claims rather than by the foregoing description. Thus, all changes which come within the meaning and range of equivalency of the claims are intended to be embraced within those claims.

What is claimed is:

1. A process for oxidizing cinchona alkaloid to its corresponding ketone comprising reacting said cinchona alkaloid with a metal ketyl in an inert hydrocarbon solvent.

2. A process according to claim 1 wherein said cinchona alkaloid is selected from the group consisting of quinine, quinidine, epiquinine, epiquinidine, and mixtures thereof.

3. A process according to claim 1 wherein said metal ketyl is prepared by the direct action of a metal on a diphenyl ketone in an inert hydrocarbon solvent under anhydrous conditions and in the absence of air.

4. The process of claim 3 wherein said metal is selected from the group consisting of sodium, potassium, and lithium.

5. A process according to claim 1 wherein said metal ketyl is prepared by reacting in a sodium amalgam with a diphenyl ketone under anhydrous conditions and in the absence of air.

6. The process of claim 3 wherein said diphenyl ketone is benzophenone or fluorenone.

7. A process according to claim 3 wherein said inert hydrocarbon solvent is the same solvent used in the oxidation of the cinchona alkaloid.

8. A process according to claim 1 wherein said inert solvent is an aromatic hydrocarbon solvent.

9. A process according to claim 8 wherein said inert solvent is selected from the group consisting of benzene, toluene, and xylene.

10. A process for oxidizing cinchona alkaloid selected from the group consisting of quinine, quinidine, epiquinine, epiquinidine and mixtures thereof comprising reacting said alkaloid with an alkali metal ketyl in a refluxing aromatic hydrocarbon solvent under anhydrous conditions.

11. A process according to claim 10 wherein said metal ketyl is prepared by the direct action of a metal on a diphenyl ketone in an inert hydrocarbon solvent under anhydrous conditions and in the absence of air.

12. The process of claim 11 wherein said metal is selected from the group consisting of sodium, potassium, and lithium.

13. A process according to claim 10 wherein said metal ketyl is prepared by reacting a sodium amalgam with a diphenyl ketone under anhydrous conditions and in the absence of air.

14. A process for preparing quininone from a cinchona alkaloid selected from the group consisting of quinine, quinidine, epiquinine, epiquinidine, and mixtures thereof comprising, reacting benzophenone or fluorenone with an alkali metal in an inert aromatic hydrocarbon solvent under anhydrous conditions to form a corresponding ketyl, and reacting said ketyl with at most a stoichiometric amount of said alkaloid in an inert aromatic hydrocarbon solvent.

15. A process according to claim 14 wherein said metal ketyl is formed by reacting metallic sodium with benzophenone in anhydrous benzene.

16. A process according to claim 15 wherein said alkaloid is quinine.

17. A process according to claim 14 wherein the same solvent is used in forming said ketyl and in reacting the ketyl with said alkaloid.

18. A process according to claim 17 wherein the solvent is selected from the group consisting of benzene, toluene, and xylene.

* * * * *